United States Patent [19]
Lanza et al.

[11] Patent Number: 5,912,005
[45] Date of Patent: *Jun. 15, 1999

[54] METHODS OF USE OF UNCOATED GEL PARTICLES

[75] Inventors: Robert P. Lanza, Natick; Willem M. Kühtreiber, Shrewsbury; William L. Chick, Wellesley, all of Mass.

[73] Assignee: BioHybrid Technologies, Inc., Shrewsbury, Mass.

[*] Notice: This patent is subject to a terminal disclaimer.

[21] Appl. No.: 08/746,970

[22] Filed: Nov. 19, 1996

Related U.S. Application Data

[63] Continuation of application No. 08/228,134, Apr. 15, 1994, Pat. No. 5,651,980.

[51] Int. Cl.$^6$ .............................. C12N 11/04; A61K 9/52
[52] U.S. Cl. .......................... 424/424; 424/422; 424/423; 435/174; 435/177; 435/243; 435/382; 514/866; 514/885; 514/907; 514/953
[58] Field of Search ................................... 435/174, 177, 435/240.22, 240.43, 243, 382; 264/4.3; 424/422, 423, 424, 489; 514/866, 907, 885, 953

[56] References Cited

U.S. PATENT DOCUMENTS

| | | | |
|---|---|---|---|
| 3,615,024 | 10/1971 | Michaels | 210/490 |
| 4,322,311 | 3/1982 | Lim et al. | 252/316 |
| 4,324,683 | 4/1982 | Lim et al. | 252/316 |
| 4,352,883 | 10/1982 | Lim | 435/178 |
| 4,353,888 | 10/1982 | Sefton | 424/25 |
| 4,391,909 | 7/1983 | Lim | 435/178 |
| 4,409,331 | 10/1983 | Lim | 435/178 |
| 4,495,288 | 1/1985 | Jarvis, Jr. et al. | 435/241 |
| 4,663,286 | 5/1987 | Tsang et al. | 435/178 |
| 4,673,566 | 6/1987 | Goosen et al. | 424/19 |
| 4,689,293 | 8/1987 | Goosen et al. | 435/1 |
| 4,690,682 | 9/1987 | Lim | 604/891 |
| 4,744,933 | 5/1988 | Rha et al. | 264/4.3 |
| 4,822,534 | 4/1989 | Lencki et al. | 264/4.3 |
| 4,902,295 | 2/1990 | Walthal et al. | 623/11 |
| 5,084,350 | 1/1992 | Chang et al. | 428/402.2 |
| 5,227,298 | 7/1993 | Weber et al. | 435/178 |
| 5,260,002 | 11/1993 | Wang | 264/4.1 |

FOREIGN PATENT DOCUMENTS

WO 93/03901  3/1993  WIPO .

OTHER PUBLICATIONS

Aebischer et al., "Macroencapsulation of dopamine–secreting cells by coextrusion with an organic polymer solution", *Biomaterials*, vol. 12 pp. 50–56 (1991).

Horcher et al., "Biocompatibility of Microbeads from Purified Alginates in Lewis–and BB–Rats", *Diabetologia*, vol. 36 Supplemental 1, Abstract 724 (1993).

Iwata et al., "Evaluation of Microencapsulated Islets in Agarose Gel as Bioartificial Pancreas by Studies of Hormone Secretion in Culture and by Xenotransplantation", *Diabetes*, vol. 38 pp. 224–225 (1989).

Iwata et al., Agarose Microcapsule Applied in Islet Xenografts (Hamster to Mouse) *Transplantation Proceedings*, vol. 24 pp. 934 (1992).

Iwata et al., "Allograft of Microencapsulated Islets in Agarose Gel in Streptozotocin–Induced and Nonobese Diabetic Mice", *Transplantation Proceedings*, vol. 24 pp. 952 (1992).

Lanza et al., "Xenotransplantation of canine, bovine and porcine islets in diabetic rats without immunosuppression", *PNAS*, vol. 88 pp. 11100–11104 (1991).

Lanza et al., "Islet Transplantation with Immunoisolation", *Diabetes*, vol. 41 pp. 1503–1510 (1992).

Lavoie et al., "Two PC12 Pheochromocytoma Lines Sealed in Hollow Fiber–Based Capsules Tonically Release L–DOPA in Vitro", *Cell Transplantation*, vol. 2 pp. 163–173 (1993).

Soon–Shiong et al., "An Immunologic Basis for the Fibrotic Reaction to Implanted Microcapsules", *Transplantation Proceedings*, vol. 23 No. 1, pp. 758–759 (1991).

Soon–Shiong et al., "Successful Reversal of Spontaneous Diabetes in Dogs by Intraperitoneal Microencapsulated Islets", *Transplantation*, vol. 54 pp. 769–774 (1992).

Soon–Shiong et al., "Long Term Reversal of Diabetes by the Injection of Immunoprotected Islets", *PNAS*, vol. 90 pp. 5843–5847 (1993).

Sugamori et al., "Microencapsulation of Pancreatic Islets in a Water Insoluble Polyacrylate", *Trans. Am. Soc. Artif. Intern. Organs*, vol. 35 pp. 791–799 (1989).

Tanaka et al., "Diffusion Characteristics of Substrates in Ca–Alginate Gel Beads", *Biotechnology and Bioengineering*, vol. 26 pp. 53–58 (1984).

Uludag et al., "Metabolic Activity and Proliferation of Cho Cells in Hydroxyethyl Methacrylate–Methyl Methacrylate (Hema–MMA) Microcapsules", *Cell Transplantation*, vol. 2 pp. 175–182 (1993).

Weber et al., "The Role of CD4+ Helper T Cells in the Destruction of Microencapsulated Islet Xenografts in Nod Mice", *Transplantation*, vol. 49 pp. 396–404 (1990).

Wiegand et al., "Macrophage–Generated Nitric Oxide as Cytotoxic Factor in Destruction of Alginate–Encapsulated Islets", *Transplantation*, vol. 56 pp. 1206–1212 (1993).

Zekorn et al., "Prolonged Graft Function After Transplantation of Microencapsulated Islets into Presensitized Recipients", *Diabetologia*, vol. 36, Supplement 1, Abstract 721 (1993).

*Primary Examiner*—S. Mark Clardy
*Attorney, Agent, or Firm*—Fish & Richardson P.C.

[57] ABSTRACT

The invention covers a method of implanting a living donor cell into a host animal without inflammatory response or rejection of the donor cell by the host animal, by obtaining an uncoated particle of a biocompatible, temperature-independent gel that encapsulates the living donor cell, wherein the uncoated particle provides a molecular weight cutoff that prevents host animal immune cells from entering the particle, yet does not have to prevent entry of host animal IgG and complement into the particle, and implanting the uncoated particle into the host animal.

64 Claims, 6 Drawing Sheets

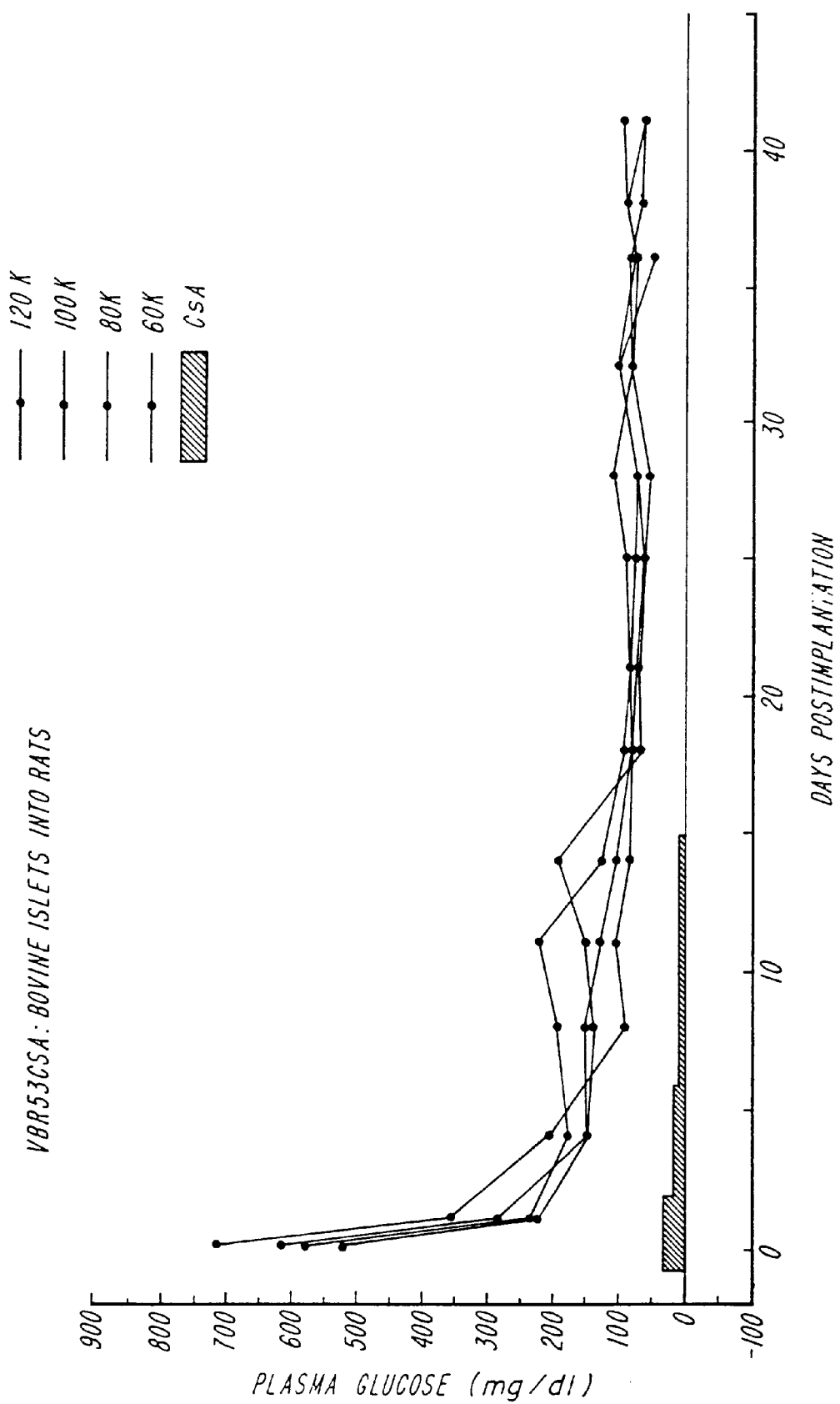

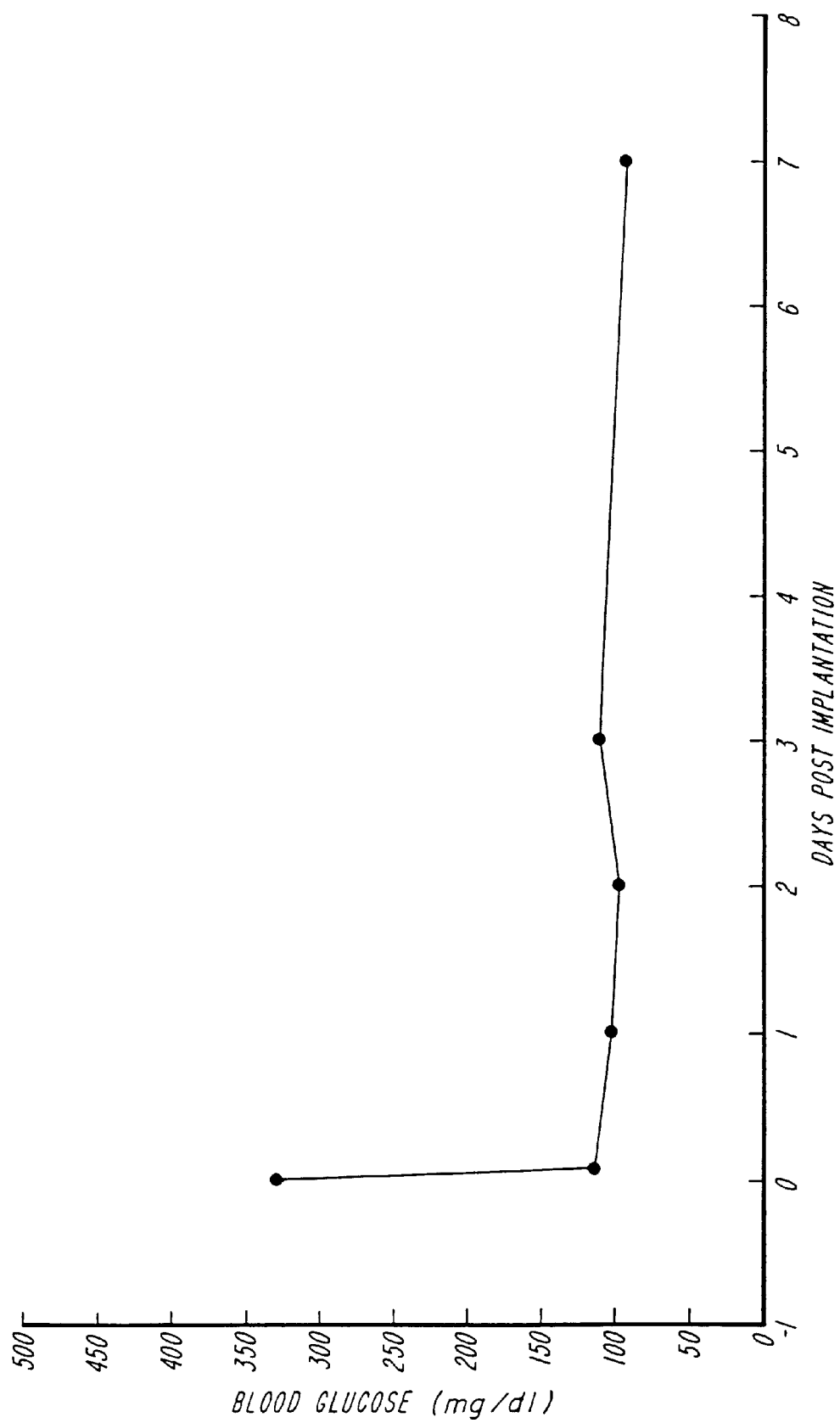

METHODS OF USE OF UNCOATED GEL PARTICLES

This application is a continuation application of Ser. No. 08/228,134 filed on Apr. 15, 1994, now U.S. Pat. No. 5,651,980. The contents of all of the aforementioned application are hereby incorporated by reference.

BACKGROUND OF THE INVENTION

The invention relates to methods of use of gel particles such as beads and spheres.

Gel microcapsules, e.g., of alginate, that contain a relatively small number of living cells have been used to transplant donor cells into host animals in both allografts, i.e., same-species transplants, and xenografts, i.e., different-species transplants. The microcapsules are used primarily in an attempt to immunoisolate the donor cells from the host's immune system. In the case of alginate microcapsules, they include an inner gel core and an outer semipermeable membrane or other coating with a controlled porosity to prevent components of the host's immune system from entering and destroying the cells within the microcapsule cores.

Several methods for microencapsulating cells, e.g., pancreatic islet cells, in alginate gels have been investigated. These include the alginate-polylysine technique described in Lim et al., U.S. Pat. No. 4,391,909 and Soon-Shiong et al., Transplantation, 54:769–774 (1992), the alginate-chitosan system described in Rha et al., U.S. Pat. No. 4,744,933, and the polyacrylate encapsulation method described in Sefton, U.S. Pat. No. 4,353,888. Each of these methods results in alginate gel microcapsules with an outer coating that is distinct from the inner core.

The alginate-polylysine technique, involves extruding a mixture of cells and sodium alginate into a $CaCl_2$ solution using a droplet generation device to form temporary gelled droplets. These droplets are then coated with positively charged polylysine to form a semipermeable outer membrane or coating around the gelled droplets. Tests have shown that these microcapsules are unstable and produce an inflammatory and fibrotic response when implanted into the peritoneal cavity of animals. However, the addition of a third outer alginate layer over the polylysine membrane has improved the biocompatibility of the microcapsules, resulting in an increase in the duration of Islet allograft function in diabetic rodents to more than a year, as described in O'Shea et al., Biochem. Biophys. Acta, 133–136 (1984).

Although the alginate-polylysine microcapsules have been shown to prolong the survival of cells in allografts and xenografts, these microcapsules have typically required adjunctive treatment with immunosuppressive agents such as cyclosporin ("CsA"). However, when used in therapeutic, i.e., immunosuppressant, dosages, these agents cause a host of serious side effects including infection, cancer, and renal toxicity. Thus, the use of immunosuppressive agents in therapeutic dosages is undesirable.

Nevertheless, immunosuppressive agents are still used. For example, Soon-Shiong et al., Transplantation, 54:769–774 (1992) and Soon-Shiong et al., P.N.A.S., USA, 90:5843–5847 (1993), describe the use of alginate-polylysine-alginate microcapsules for allografts of canine islets into diabetic dogs, both with continuous or temporary, e.g., 30 day, immunosuppression with CsA. Both sets of dogs remained independent of insulin for an average of over 100 days.

In another report, Soon-Shiong et al., First Int'l Cong. Xenotrans., p. 22 (Minneapolis, Minn. 1991), describes the prolongation of discordant islet xenograft function in streptozotocin-induced diabetic rats by alginate-polylysine microencapsulation. Microencapsulated canine and human islets were implanted intraperitoneally in the rats and compared to nonencapsulated islet implants. Low dose CsA therapy was instituted in both groups for the duration of the study. Euglycemia was maintained for 43 to 123 days for canine islets, and 42 to 136 days for human islets. In contrast, nonencapsulated islets achieved euglycemia for less than 2 days.

However, there are a few reports of uses of microcapsules without immunosuppression. For example, Weber et al. Transplantation, 49:396–404 (1990), describes a discordant, e.g., from unrelated species, menograft in which alginate-polylysine microcapsules containing canine islets functioned for an average of only 11.5≅3 days in diabetic NOD mice. However, immunosuppressive treatment with anti-CD4 monoclonal antibody allowed the cells in some of the recipient mice to remain functional for an average of 83 days.

In addition, Iwata et al., Diabetes, 38 (Supp. 1):224–25 (1988)e describes the use of pancreatic islet cells encapsulated in agarose gel microspheres in concordant xenografts, i.e., transplants from different, but closely related species, e.g., rodent-to-rodent transplants, such as hamster cells into mice. No immunosuppressive agent was used in this study, and the two mice remained normoglycemic for 29 and 53 days, respectively.

In a second similar concordant xenograft study, Iwata et al., Transplantation Proc., 24:952 (1992), the immunosuppressive effect of the drug 15-deoxyspergualin on host mice was compared with control mice that received no immunosuppression. Iwata et al. concluded that the agarose microspheres without immunosuppression could not effectively protect the concordant xenografts from rejection, because blood glucose levels indicated that only 2 of 8 xenografts survived over 100 days. However, blood glucose levels indicated that 3 of 5 xenografts survived over 100 days in mice receiving the immunosuppressive drug for 120 days (2.5 mg/kg/day) or 40 days (5.0 mg/kg/day).

In another study Iwata at al. Transplantation Proc., 24:934 (1992), used mouse islet allografts in agarose microspheres to achieve normoglycemia in diabetic mice without immunosuppression. Blood glucose levels indicated that the majority of these allografts survived over 100 days.

SUMMARY OF THE INVENTION

The present methods of using biocompatible, temperature-independent gel particles, e.g., beads, are based on the discovery that donor cells, e.g., porcine, bovine, or canine islet cells, encapsulated in alginate beads can be successfully transplanted into a host animal, e.g., mouse, rat, or dog, without any protective coating or semipermeable membrane around the beads, and with the use of only minimal doses, if any, of immunosuppressive or anti-inflammatory drugs. These simple, uncoated beads can be implanted into the host and provide effective immunoisolation of the encapsulated cells without eliciting a fibrotic response or a host immune rejection of the donor cells within the beads.

In general, the invention features a method of implanting a living donor cell into a host animal without inflammatory response or rejection of the donor cell by the host animal by obtaining an uncoated particle consisting essentially of a biocompatible, temperature-independent gel that encapsulates the living donor cell, wherein the uncoated particle provides a molecular weight cutoff that prevents host animal immune cells from entering the particle, and does not prevent entry of host animal IgG and complement into the particle, and implanting the uncoated particle Into the host animal.

As used herein, a "temperature-independent gel" is a gel that can be gelled or crosslinked, e.g., by the addition of ions such as calcium, potassium, or barium ions, without a change in temperature. An "uncoated particles" refers to a bead, sphere, or other gel structure, e.g., a cylinder, that is composed of a biocompatible, temperature-independent gel matrix without any surface or intermediate layer, e.g., in the form of a semipermeable membrane, of a permeability and molecular weight cutoff different from that of the gel matrix itself.

As used herein, "molecular weight cutoff" refers to the size of the largest molecule that is not substantially blocked by a semipermeable membrane surrounding a microcapsule or by the gel matrix itself in an uncoated gel particle, e.g., bead, according to the invention. Molecules with a molecular weight above the cutoff are substantially prevented from entering or leaving the microcapsule or gel particle. The coatings of prior art alginate microcapsules generally provide a molecular weight cutoff of greater than 50,000 and less than 100,000 daltons. The uncoated gel particles of the invention have a molecular weight cutoff of greater than about 500,000 daltons, i.e., molecules like IgG and complement can enter these gel particles, but host cells such as immunocytes are prevented from entering these gel particles. In addition, this high molecular weight cutoff allows molecules secreted by the encapsulated cells, e.g., Factor VIII or hormones, to exit the gel particles.

The invention also features a method of implanting a living donor cell into a host animal without inflammatory response or rejection of the donor cell by the host animal by suspending the living donor cell in a liquid medium, the medium consisting essentially of water and a biocompatible, temperature-independent liquid gel, forming a droplet of the liquid medium that contains at least one living cell, solidifying the droplet to form a gel particle that encapsulates the living cell, whereby no outer coating is formed on the particle, and wherein the uncoated particle provides a molecular weight cutoff that prevents host animal immune cells from entering the particle, and does not prevent entry of host animal IgG and complement into the particle, and implanting the uncoated particle into the host.

In particular embodiments, when the liquid medium contains pancreatic islets, they can be present at a density of about 2 to 60 islets per mm$^3$, and more preferably at a density of about 10 to 35 islets per mm$^3$, i.e., 10,000 to 35,000 islets per milliliter of the medium. When the liquid medium contains other living cells, they can be present at a density of about $10^5$ to $10^8$ cells, and preferably $10^6$ to $10^7$ cells, per milliliter of the medium. The density depends on the size and metabolism of the individual islets.

Furthermore, the invention features a method of treating a disease in a patient caused by a deficient production of a substance in the patient by obtaining an uncoated particle consisting essentially of a biocompatible, temperature-independent gel that encapsulates a living donor cell that secretes the substance, wherein the uncoated particle provides a molecular weight cutoff that prevents patient immune cells from entering the particle, and does not prevent entry of patient IgG and complement into the particle, and implanting the uncoated particle into the patient in a location and in a manner that allows the living cell to remain physiologically active and secrete the substance into the patient to treat the disease. For example, the uncoated particles can be implanted into an immunoprivileged site in the patient.

In particular embodiments, the disease is diabetes and the donor cell is a pancreatic islet cell. The donor cell can be selected to secrete Factor IX, Factor VIII, an interleukin, an interferon, an endocrine hormone, a nerve growth factor, tumor necrosis factor alpha, a neurotropic factor, or a neurotransmitter. The disease can be diabetes mellitus, hepatic disease, amyotrophic lateral sclerosis, hemophilia, hypothyroidism, Parkinson's disease, acquired immune deficiency syndrome, Duchenne's muscular dystrophy, infertility, epilepsy, Huntington's disease, hypoparathyroidism, a mood disorder, a motor neuron disease, osteoporosis, or Alzheimer's disease.

The invention also features an in vivo method of culturing a living cell by encapsulating the living cell in an uncoated particle consisting essentially of a biocompatible, temperature-independent gel, inserting the uncoated particle into an animal, and allowing the animal to thrive, thereby culturing the cell.

The invention further features, an in vitro method of culturing a living cell by encapsulating the living cell in an uncoated particle consisting essentially of a biocompatible, temperature-independent gel, placing the uncoated particle into a medium including nutrients and oxygen, and maintaining a sufficient amount of nutrients and oxygen in the medium to allow the cell to thrive, thereby culturing the cell.

In addition, the invention features a method of manufacturing uncoated, temperature-independent gel particles containing living cells consisting of the steps of suspending the living cells in a liquid medium, the medium consisting essentially of water and a biocompatible, temperature-independent, liquid gel, forming a droplet of the liquid medium, solidifying the droplet to form a gel particle that encapsulates the living cells, whereby no outer coating is formed on the particle, and storing the gelled uncoated particles in a nutrient medium to maintain the viability of the living cells.

In all of these methods, the living donor cell can be obtained from a species that is the same as or different from the host animal, and can be a genetically altered human cell. The host animal can be a dog or a human. The donor cell can be a porcine, bovine, canine, bacterial, fungal, or plant cell. In particular, the donor cell can be a pancreatic islet cell, or can secrete Factor IX, Factor VIII, an interleukin, an interferon, an endocrine hormone, a nerve growth factor, tumor necrosis factor alpha, a neurotropic factor, or a neurotransmitter.

In particular embodiments, the gel particle is spherical and has a diameter of from 50 to 6000 microns, and preferably from 2000 to 4500 microns. The gel can be an alginate or alginate derivative, and the alginate can be crosslinked with an ion, such as the calcium in a calcium salt. The uncoated gel particle can be biodegradable, and the rate of degradation of the gel in the uncoated particle can be selected to match the life expectancy of the donor cell.

In other embodiments, the uncoated particle encapsulates an autologous erythrocyte in addition to the donor cell, or can be treated with a nitric oxide inhibitor prior to implantation. In addition, the method can include the step of administering a drug to the host animal at a dosage effective to inhibit fibrosis and inflammation of the uncoated particle, but at a dosage lower than that required to achieve immunosuppression when the donor cell is implanted into the host animal without encapsulation. For example, the drug can be cyclosporin A and is administered at a dosage that achieves a whole blood trough level of less than about 100 ng/ml in the host animal. In addition, the drug can be administered for up to several weeks, e.g., one month, or longer, after implantation, and is then no longer administered.

The invention also provides a variety of other features which enhance implant function and longevity including size of the beads, types of gel matrices, and for islet cells, optimum cell densities. It is essential that the gel matrices keep host cells, i.e., immunocytes, physically separated from the donor tissue cells. It is also important that the particles have a sufficient size to keep antigens secreted by the encapsulated living cells from building up in the matrix and coming into direct contact with the host, and to protect the encapsulated donor cells from small soluble or cytotoxic factors in the host such as nitric oxide, lymphokines, cytokines, and natural killer (NK) cytotoxic factors. The charge and chemical properties of the matrix are also important in this respect.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the following detailed description and from the claims.

BRIEF DESCRIPTION OF THE DRAWINGS

FIGS. 4 is a graph showing the effect of bovine islet implants on plasma glucose level in rats.

FIGS. 5A and 5B are graphs showing the blood glucose level in diabetic patient dogs before and after implantation of canine islets with low dose cyclosporin.

DETAILED DESCRIPTION

Figure 1:
FIG. 1 is a photomicrograph of a mouse macrophage digesting a 18 day old, fibrosed alginate gel bead (fibers in cells.

Various types of donor cells can be isolated, encapsulated, and then implanted into a host according to the present invention.

Isolation of Cells

Cells are isolated from surrounding tissues or grown in culture by procedures known to the art, and are then suspended in a liquid medium prior to encapsulation. For example, pancreatic islet cells were prepared from either adult mongrel dogs, pigs, or bovine calves (0–2 weeks old) by a modification of the methods of Warnock and Rajotte, Diabetes, 37:467 (1988), as previously described in Lanza et al., P.N.A.S. USA, 88:11100–11104 (1991).

Briefly, aseptic, viable porcine pancreata were obtained under aseptic operating room procedures. After resection (warm ischemia for less than about 15 minutes), the glands were cannulated and infused with cold (4° C.) University of Wisconsin (UW) organ preservation solution. Pancreatic tissues were dissociated using an intraductal collagenase digestion procedure The collagenase is delivered by peristaltic pump, and the digested pancreas is mechanically disrupted in a polypropylene dissociation chamber containing 2–6 mm glass beads. The islets were separated from the exocrine tissue by discontinuous density gradient centrifugation (27%, 20.5%, and 11% (w/v) FICOLL® (Sigma, F 9378) in Eurocollins solution).

Isolated islets were then cultured for one day either in M199/Earle's medium supplemented with 10% (vol/vol) fetal bovine serum, 30 mN HEPES, 100 mg/dl glucose, and 400 IU/ml penicillin (canine), or in α-HEN plus 10% heat-inactivated horse serum (bovine and porcine) in a humidified atmosphere of 5% $CO_2$/95% air at 37° C. A typical yield of islets should be in the range of $0.5–1.8 \times 10^6$ islets for adult pancreas (400 gm wet weight, islet diameter 80–125 μm, purity 85–95%, viability greater than 90% (see below). The cells may also be isolated by other procedures and cultured under other suitable conditions.

Ischemic deterioration of the islet cells is minimized by using tissue fragments of a suitable size, e.g., islet fragments should be less than about 120 microns, and preferably 40 to 100 microns, in diameter Viability, growth, longevity, and/or function of the islet cells can be enhanced by co-culturing, i.e., by mixing other cell types in the liquid medium-prior to encapsulation. Useful cell types include cells which secrete growth hormone, e.g., GH-3 cells, or cells which secrete connective tissue and/or extracellular matrix components, e.g., fibroblasts and endothelial cells. In addition, cells e.g., islets, can be co-cultured with red blood cells, hemoglobin, or other oxygen carrying agents to enhance oxygen availability.

Islet quality control procedures are used to enable comparison of different lots of islets prepared at different times. Purity amount of islet tissue compared to exocrine tissue contamination) depends on the relatively unique characteristic of pancreatic islets to rapidly take up diphenyl thiocarbazone (dithizone). Islets are therefore incubated for five to ten minutes with 50 μg/ml of dithizone (D5130, Sigma) to stain them red. The preparation is then examined under light microscopy for a qualitative estimate of purity. Quantification of purity is effected by islet dispersion and counting of stained and unstained cells, or with a spectrophotometric assay of dithizone uptake/μg DNA.

Viability can be determined by any one of several assays that depend on the capability of viable cells to exclude certain dyes. For example, one assay uses a combination of the fluorescent stains acridine orange, which stains only viable cells green, and propidium iodide, which stains only the nuclei of dead cells red. The islets are incubated with the dyes (acridine orange, Sigma A6014, 50 μg/ml, and propidium iodide, Sigma P4170, 2.5 μg/ml) in a PBS solution for 10 to 15 minutes and then dispersed into single cells. Counts of red and green fluorescing cells are used to calculate % Viability.

Insulin secretory activity of the islets is determined both in static culture, e.g., expressed as units of insulin per islet volume, and based on the capability of the islets to respond to graded concentrations of glucose. These values are quantitatively established by measuring the insulin secreted by islets exposed to a range of glucose concentrations extending from 2.8 to 28 mM glucose.

Encapsulation

Once the cells are isolated and suspended in liquid medium, they must be encapsulated by a supporting gel matrix. Beads suitable for implantation into a host animal include a number of living donor cells in a gel matrix without any protective coating. Using standard techniques, a gel matrix is formed by adding cells, e.g., pancreatic islets, to a solution of nutrient medium and liquified gel, e.g., sodium alginate, to form a suspension, and then crosslinking the gel, e.g., by adding a crosslinking agent such as calcium chloride. The gel matrix can be any one or a combination of a variety of substances that are biocompatible with the host animal, and are capable of maintaining cellular viability and physically supporting the tissue or cells in suspension, as long as they have the required concentration and purity.

The gels must be temperature-independent, in that they can be gelled or crosslinked, e.g., by the addition of ions such as calcium, potassium, or barium ions, without a change in temperature, which could be harmful or fatal to the living cells to be encapsulated. Temperature-independent gels include alginates, carrageenans, and gums such as xanthan gum. As used herein, the term alginate includes alginate derivatives. These gels should be treated to remove polyphenols, lipopolysaccharides, endotoxins, and other impurities using standard techniques.

Alginate is composed of blocks of 1,4 linked β-D-mannuronic acid (M) and α-1-guluronic acid (G) linked together, e.g., in alternating MG blocks. The preferred alginate is one formulated with a high G block content, e.g., at least about 60 percent. The higher the percentage of G blocks the greater the pore size and the strength of the gel matrix. In addition, it has been noted that alginate gels with a high M block content appear to be more immunogenic than gels with a high G block content. See, e.g., Soon-Shiong et al., *Transplant. Proc.* 23 758–759 (1991)e and Soon-Shiong et al., *Transplantation*, 54:769–774 (1992).

The gel matrix should be sufficiently viscous to maintain the cells in a dispersed state. When alginate is used as the gel matrix, it is added up to about 3% preferably to about 1 to 2%, of the liquid medium, and the solution is cross-linked to form a semisolid gel in which the cells are suspended. These percentages provide a matrix that maintains its shape and has sufficient mechanical strength to remain intact in vivo for several months.

For example, pancreatic islets can be encapsulated as follows. After preculturing overnight, islet cells were suspended uniformly at a density of 20,000 islets/ml, which is 20 islets/mm$^3$, in a solution of 1.5% (wt/vol) Pronova LVG sodium alginate (Protan, Drammen, Norway) in culture medium plus additives (α-MEM, 10 mM HEPES pH 7.1, penicillin, 2 mM glutamine for porcine islets; and M199 with the same additives for canine islets). A syringe pump was used to pump the suspension through an air jet apparatus (containing a straight-edged 22 gauge needle) at a speed of 3 ml/min. Droplets formed at the tip of the needle were stripped off by means of a concentric flow of air at an air speed of 7 to 8 m/sec. The resulting droplets fell a distance of 4 cm and were collected in a solution of 1.5% $CaCl_2$ in 10 mM HEPES (pH 7.1) to form gelled beads. These beads can be made in various sizes ranging from about 700 μm to 3500 μm in diameter by altering the air flow speed, the faster the flow rate the smaller the beads.

Each bead contains approximately 1 to 25 islets. After three minutes, the beads were washed three times with culture medium (appropriate for the species of islets in use), and were then cultured in a tissue culture incubator at 37° C. and 5% $CO_2$ until they were implanted.

Larger beads up to 3500 to 6000 mm in diameter, were or can be made in a similar manner, or can be extruded through a syringe with a 14 gauge catheter. Beads can also be made by other standard techniques, as long as the resulting beads have the preferred characteristics described below.

The beads were cultured in vitro for up to four weeks, and the insulin secretion compared to free islets, prepared as described above. The insulin secretory response of the beads was approximately 50 to 80% of that of the free islets. Histological examination at four weeks revealed viable endocrine tissue within the beads. The islets were morphologically intact, and contained well granulated β-cells.

Specific Parameters for Uncoated Particles

The particles, e.g., beads, are preferably spherical in configuration and have a diameter of about 600 to 6000 μm, preferably 1500 to 3500 μm. Particles as small as 50 μm can be made. The preferred size is based on diffusion distances from the surface of the bead to the cells within. In addition, smaller beads, e.g., 700 to 900 μm are suitable for allographic transplants, whereas larger beads, e.g., 2000 to 5000 μm, are preferred for xenographic transplants.

A spherical shape is preferred for the beads to present a smooth outer surface without edges, which tends to inhibit fibrotic encapsulation of the beads. The beads may be designed to be more or less biodegradable depending on the intended use. For example, if the beads are intended to break down within a certain period of time, materials such as cellulose or collagen can be added to the gel matrix to facilitate the breakdown. However, as shown in FIG. 1, applicants have discovered that even pure alginate beads are attacked and digested by macrophages after the gel particle has been coated by fibrotic tissue by the host. FIG. 1 shows a macrophage with alginte fibers in the center of the cell. Other degradative mechanisms also occur. The resulting breakdown products are resorbed by the body, or excreted in the urine as segments of crosslinked or uncrosslinked alginate molecules. This breakdown of the beads may start within a few weeks or months, or within a year, and is controlled by the size of the beads, the crosslinking agent used to form the beads, and the added ingredients such as collagen, which dissolves on its own to weaken the bead structure after a few weeks. In general, this breakdown typically occurs after 6 to 12 months.

Other characteristics of the uncoated beads include (1) morphological and chemical properties, e.g., the smoothness of surface, the structure of the matrix, and the ability to react with other chemical substances, and (2) transport properties, e.g., permeability to microsolutes, nutrients, $O_2$ wastes, macrosolutes (e.g., insulin), essential proteins, and molecular weight cutoff to prevent immune cells (lymphocytes/macrophages) from entering the bead as discussed above. Both the morphological and transport characteristics are achieved by the gel matrix which physically isolates the donor cells from the host cells and allows nutrients and oxygen to flow freely into the matrix, which facilitates viability of cells. In addition, the negative charge of some gels, e.g., sodium alginate, should aid in preventing proteins of the humoral immune response (complement/cytokines) from entering the gel particles.

Donor Cell and Host Characteristics

The living donor cells are preferably mammalian cells, but can also be bacterial, fungal, or plant cells that express or secrete a desired protein hormones, or other substance. The characteristics of these encapsulated donor cells are important to the survival of cells in the particles once implanted into a host. For example, the total antigenic load should be kept as low as possible while still implanting a sufficient number of donor cells to achieve the desired therapeutic effect.

This antigenic load can be controlled by adjusting the density of cells per bead and/or by adjusting the total number of beads implanted into the host. These numbers vary depending on the cell type and the type of host. For example, in a dog example described below, diabetes was treated with beads made from 32.0 ml of gel containing porcine islets at a density of about 20 per mm$^3$. To standardize islet dosages the EIN (equivalent islet number) can be used. This number is based on the islet volume of a standard islet of 150 microns in diameter.

The total EIN implanted into a patient depends on the insulin requirements of the patient, and on the metabolism, type, and quality of the islets, which is determined by in vitro tests of the encapsulated islets prior to implantation as described herein. For example, it is known that porcine islets produce more insulin than bovine or canine islets. The amount of insulin (insulin units) required by a patient is determined empirically on an individual basis, and is based on sugar levels monitored several times per day. For example, diabetic dogs may require about 5 to 40 units of insulin per day, whereas a typical human diabetic patient may require 20 to 50 units per day. In all cases, these amounts depend on the severity of the disease, diet, exercise, and other factors. About 1.0 to 2.5 million porcine islets are required to achieve this level of insulin production for a human patient.

In addition, the immunogenicity of the donor cells must be considered. For example, it is believed that fetal or neonatal tissue will provoke less of a host reaction than adult tissue. The donor tissue can also be modulated to reduce its immunogenicity prior to implantation, e.g., by organ culture, UV irradiation, and/or pretreatment with antibodies to mask the antigens on the surface of the donor cells. Organ culturing selectively removes dendritic cells (antigen presenting cells) from the donor tissue since they die faster than other cells in culture. Culture conditions such as high oxygen and low temperature are effective to selectively destroy the more sensitive dendritic cells. All of these methods of modulating donor tissues are described in Chapters 9, 10, 11 of Lanza et al. (eds.), *Immunomodulation of Pancreatic Islets* (RG Landes, Tex., 1994), which is incorporated herein by reference.

The immune system of the host can also be modulated prior to or after implantation of the encapsulated donor cells to ensure survival of the implanted cells. Allografts in mammals larger than mice or rats require a short course of an immunosuppressant or anti-inflammatory drug at a low dosage. Discordant xenografts with small beads, e.g., 700 to 900 μm in diameter, in larger mammals such as humans also require adjunctive immunosuppression. As discussed below, minimal or no immunosuoppression or anti-inflammatory therapy is necessary with larger beads.

Immunosuppressant drugs include cyclosporine A ("CsA"), FK-506, and deoxyspergualin. Anti-inflammatory/anti-fibrosis drugs include steroidal drugs such as prednisone, and non-steroidal drugs such a s ibuprofen and aspirin. Certain immunosuppressants such as CsA have an anti-fibrosis effect at very low, "subtherapeutic" doses, e.g., at a so-called "whole blood trough level" of less than 100 ng/ml when analyzed by HPLC. Initial doses can be higher, e.g., up to a few hundred ng/ml, without attaining a therapeutic, e.g., immunosuppressive, dose, which is in the range of 550 to 900 ng/ml in dogs for unencapsulated xenogeneic islets. Thus, CsA can be used as an effective anti-fibrotic without the need for any other drugs. The maintenance blood levels of less than 100 ng/ml, e.g., 30 ng/ml, in allografts can be discontinued within several weeks to less than three months.

In human patients, the maximum therapeutic dosage of CsA should be less than 800 ng/ml to avoid toxicity problems. However, according to the invention, only low doses, e.g., an initial dosage of an immunosuppressive/anti-fibrotic agent of a few hundred ng/ml, and then a maintenance dosage of less than 100 ng/ml, should be administered.

In addition, according to in vitro observations, the living donor cells within the gel beads can be protected from cytotoxic nitric oxide radicals, by co-encapsulating the cells with autologous erythrocytes, which scavenge nitric oxide that may enter the gel beads once implanted, e.g., as described in Wiegand et al., *Transplantation,* 56:1206–1212 (November 1993). In addition, the gel beads can be treated with nitric oxide inhibitors such as $N^G$-methyl-L-arginine prior to implantation to provide a protective effect.

Implantation

The beads can be simply implanted into a host by injection with a standard catheter or syringe, e.g., with a 16 gauge needle for beads less than 1000 μm in diameter. Larger beads can be inserted via a small incision, e.g., with a catheter or funnel-like device. The beads are preferably implanted into the host intraperitoneally. The beads can also be implanted intramuscularly or subcutaneously. Alternatively, the beads can also be implanted into immunoprivileged sites such as the brain, testes, or thymus, where the host's immune response is least vigorous, as described in Chapter 7 of Lanza et al. (eds.), *Immunomodulation of Pancreatic Islets* (RG Landes, Tex., 1994). In addition, the beads can be inserted through a small surgically created opening using a gun/trocar type device that slips the beads under the skin.

EXAMPLES

Implantation of Porcine Pancreatic Islets into Mice and Rats

To determine whether encapsulated pancreatic islet cells can function, e.g., secrete insulin in a host animal, over extended periods of time, 800±100 μm diameter beads, containing a total of between 10K and 100K islets per animal, were implanted as discordant xenografts into mouse and rat diabetes mellitus models. Adult male Lewis rate (Charles River, Wilmington, Mass.) weighing 250 to 300 g, and C57BL/6J mice weighing about 20 to 30 g were used as implant hosts. Diabetes mellitus was induced in these animals by a single injection of streptozotocin ("STZ") ten to fourteen days prior to implantation of the beads. Rats were injected with 42 mg/kg body weight of STZ into the tail vein. Mice were injected with 165 mg/kg body weight of STZ into the peritoneal cavity.

Fasting plasma glucose concentrations (mg per dl) were measured by tail bleedings from both animals using a glucose oxidase method (Backman Glucose Analyzer 2, Fullerton, Calif.) Determinations were performed thrice weekly for one month, and then weekly for the duration of each study. Failure of the encapsulated islets to reverse hyperglycemia was considered to have occurred when glucose concentrations exceeded 250 mg per dl on two consecutive testings.

Host animals were anesthetized with ketamine/xylazine (rats, 0.5 μl/g i.m.; mice, 5.0–7.5 μl/g i.p.) prior to implantation. The porcine islets were isolated and encapsulated in 800 μm diameter beads as described above. Between 10K and 100K islets were implanted into the peritoneal cavity of the rats or mice either with a 16 gauge catheter or through a small (1–2 cm) midline incision. This corresponds to a total of about 0.5 to 5.0 mls of gel which is formed into the beads, i.e., the islets are present in the gel at a density of about 20K islets/ml of gel. The wound was closed in two layers with 4-0 silk suture. No immunosuppressive drugs were used.

As discussed below, the beads generally reversed hyperglycemia in the hosts. This condition was confirmed by histological analysis. The encapsulated islets were recovered from streptozotocin-induced diabetic animals sacrificed two weeks after implantation and were routinely fixed and examined histologically. Donor islets were fixed in Bouin's solution, and then dehydrated and embedded in paraffin by routine histologic methods. The tissue was sectioned serially (5 $\mu$m sections) and stained with hematoxylin-eosin. The presence of insulin, glucagon, and somatostatin in donor islets was determined using immunoperoxidase histochemistry as described in Warnke et al., *J. Histochem. Cytochem*, 28:771 (1980) or Like et al., *Lab. Invest.*; 38:340 (1978). These tests are used to determine whether all these hormone-secreting cell types in the islets are viable.

Such histological tests are the only accurate method to determine the viability of islets after implantation in chemically induced diabetic animals, because it is common for such animals to revert to a non-diabetic state, which gives a false indication of islet viability if determined only by blood tests such as blood glucose levels. In addition, blood tests provide no indication of fibrosis.

Figure 2:
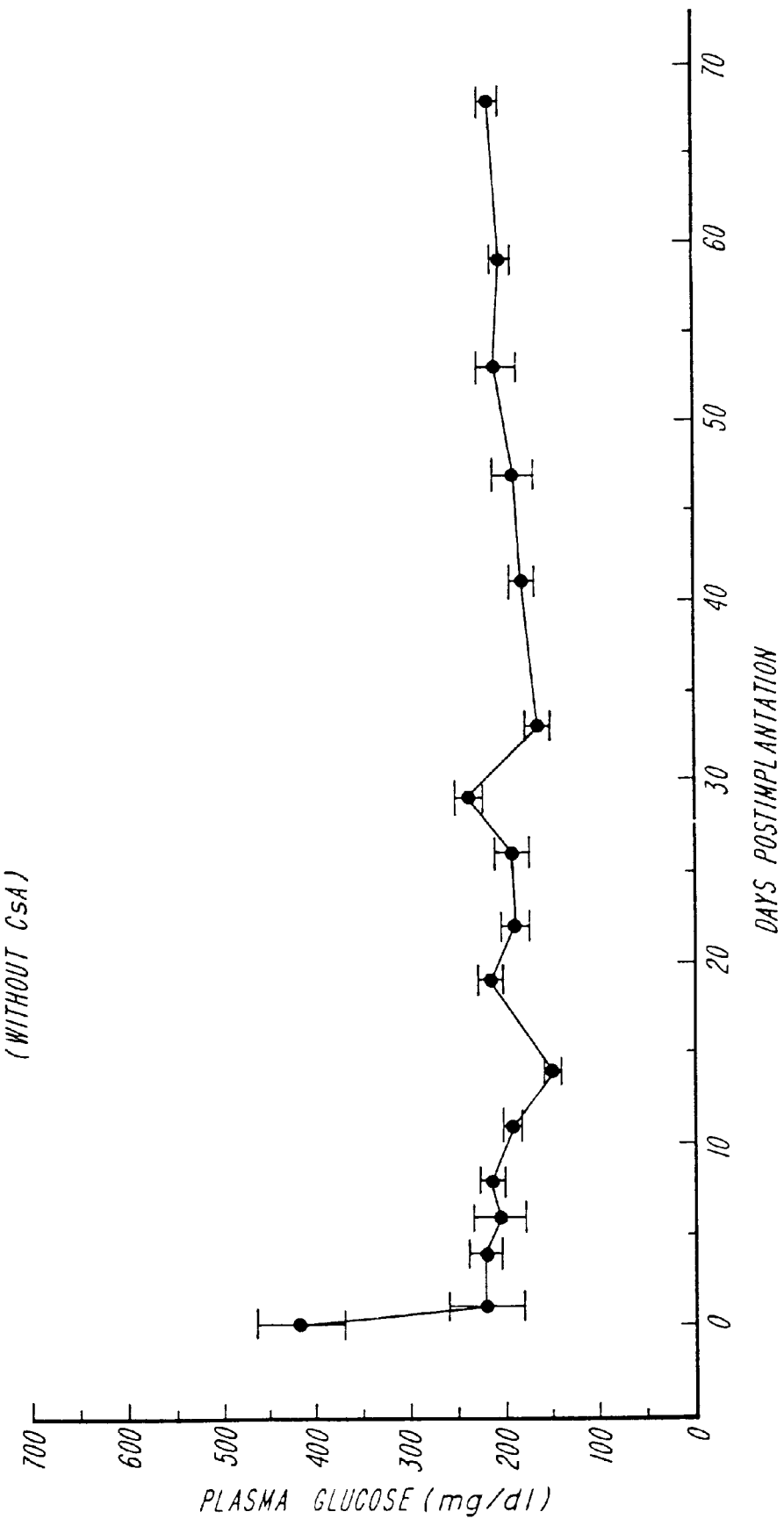
FIG. 2 is a graph showing the effect of porcine islet implants on plasma glucose level in mice.

As shown in FIG. 2, porcine islets (approximately 20,000) encapsulated in 800±100 $\mu$m diameter beads made from 1.0 ml of alginate gel, and implanted into diabetic mice reversed hyperglycemia for more than 10 weeks as evidenced by a drop in the plasma glucose level immediately after implantation from about 400 to 450 mg/dl to about 200 mg/dl, and the maintenance of the plasma glucose level at about 200 to 250 mg/dl.

These results were confirmed by histological analysis, which demonstrated intact, viable islets after 10 weeks. In addition, the beads showed little or no fibrosis for the 10 week period. Control experiments in which approximately 100,000 non-encapsulation canine, bovine, or porcine islets were implanted intraperitoneally into STZ-induced diabetic Lewis rats showed that these xenografts all failed within one week.

In other experiments, porcine islets were. immobilized in five different sizes of uncoated alginate beads (880, 1600, 2200, 3000, and 3700 $\mu$m in diameter). These were implanted into the peritoneal cavity of STZ-induced diabetic rats for 11 to 14 days (n=2 for all tests). No immunosuppressant was used in these experiments. No islets survived in any of the 800 $\mu$m or 1600 $\mu$m diameter beads. Thus, it appears that smaller diameter beads containing porcine islets do not work without immunosuppression in rats. In other experiments, loss of blood glucose control and histology confirm that smaller diameter gel beads are rejected within about 6 to 10 days after implantation.

However, discordant xenograft studies using larger beads, e.g., 2200, 3000, and 3700 $\mu$m diameter beads, showed that porcine islet cells remained viable for more than four weeks in rats without any immunosuppression. The results (percent viability after 4 weeks) are shown in Table 1 below.

TABLE 1

| Uncoated Bead Diameter ($\mu$m) | Percent Viability |
|---|---|
| 800 | 0 |
| 1600 | 0 |
| 2200 | 33 to 44 |
| 3000 | 50 to 75 |
| 3700 | 80 to 85 |

Thus, larger diameter beads are successful in protecting the donor porcine islets from the host rats' immune systems without any immunosuppressant or anti-fibrotic drugs.

Implantation of Bovine Pancreatic Islets into Mice and Rats

Figure 3:
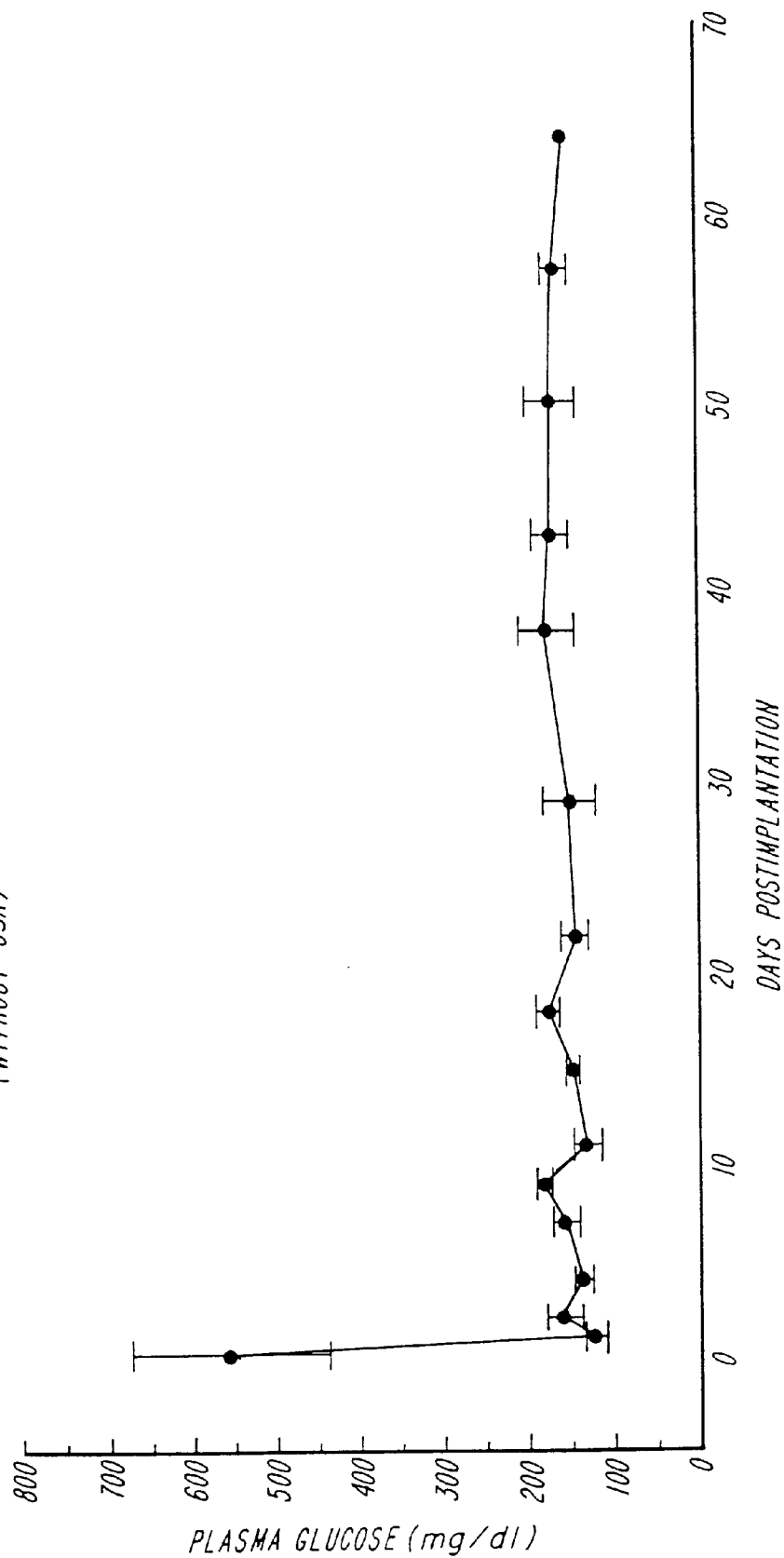
FIG. 3 is a graph showing the effect of bovine islet implants on plasma glucose level in mice.

In another discordant xenograft study, bovine calf pancreatic islet cells were isolated and encapsulated as described above for the porcine islets. Again, these beads were analyzed in the mouse and rat diabetes mellitus model described above. As shown in FIG. 3, bovine islets (approximately 20,000) encapsulated in 800±100 $\mu$m diameter beads made from 1.0 ml of alginate gel, and implanted into mice reversed hyperglycemia for greater than 60 days as evidenced by the immediate drop in plasma glucose level after implantation from about 550 mg/dl to about 150 mg/dl, and the maintenance of this level for the duration of the study Histological analysis demonstrated intact, viable islets for more than 60 days with little or no fibrosis.

Similarly, different numbers of encapsulated bovine islets were implanted into rats. CsA was administered subcutaneously to the rats for the first two weeks of the study and then discontinued (30 mg/kg on days −1, 0, and 1; 15 mg/kg on days 2 to 5; and 7 mg/kg on days 6 to 14 ). As shown in FIG. 4, all four dosage levels of islets (60K, 80K, 100K, and 120K) reversed hyperglycemia for more than 40 days. Plasma glucose levels fell from about 525 to 725 mg/dl to less than 250 mg/dl after implantation, and maintained these levels for the duration of the study.

Histological analysis demonstrated intact, viable islets at 64 days, with little or no fibrosis.

Implantation of Islet Cells into Dogs

In an allograft study, donor canine islets (approximately 100,000) were encapsulated in 800±100 $\mu$m diameter beads made from 5.0 ml of alginate gel and implanted into dog hosts. Although such allografts are normally rejected by a host within 7 days, the encapsulated donor islets were all viable after three weeks. One dog received no immunosuppressant drug, and another received one daily injection of 10 mg/kg CsA, which provides a blood trough level of about 200 to 300 ng/ml, depending on the actual time of administration, liver function, and time of measurement. There was no fibrosis of the implanted beads in either dog, even without the use of any immunosuppressive agent in one of the dogs. Histology showed that 50% of the islets were viable in both dogs after three weeks. Thus, the allografts were successful with or without the use of immunosuppressant or anti-fibrotic drugs.

In a discordant xenograft dog study, porcine pancreatic islets (approximately 140,000) were isolated and encapsulated in 800±100 $\mu$m beads made from 7.0 ml of alginate gel and implanted as described above for the porcine islets. These beads were analyzed in a normal dog. The immunosuppressant CsA was administered orally to the dog at a dosage of 10 mg/kg/day throughout the course of the study. Histological analysis showed some viable islets after three weeks.

As a control, empty beads of the same size were injected into dogs to determine whether the beads themselves caused any inflammation or other immune reaction in the host. Histological examination showed that neither the empty nor the islet-containing beads had developed any fibrosis after over one month inside the dog host.

Treatment of Diabetic Dogs

Figure 5A:
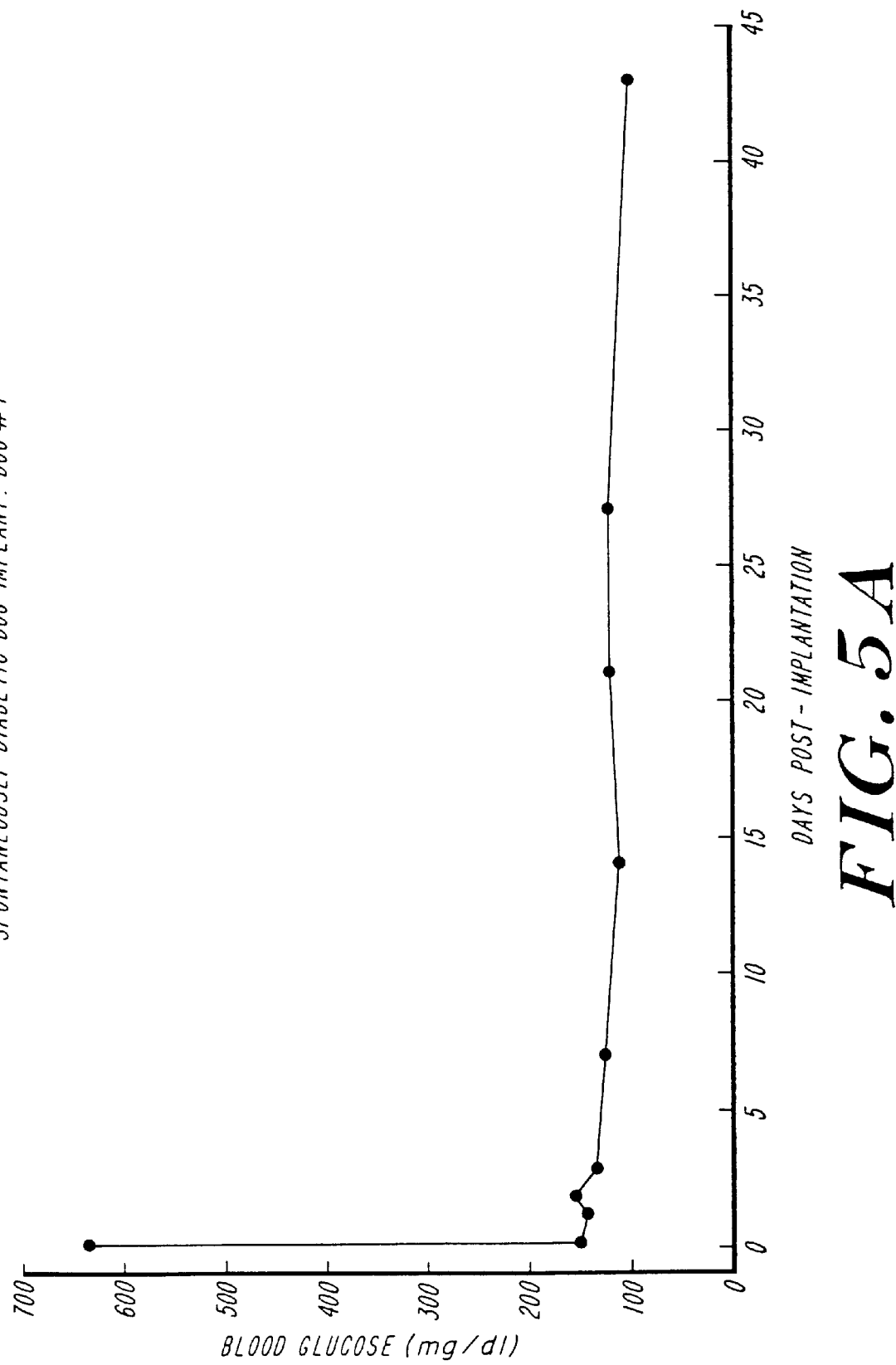

In another dog study, two actual diabetic patient dogs were treated by implantation of about 600,00 to 650,000 canine islets in 800±100 μm beads made from 30.0 to 33.0 ml of alginate gel and implanted as described above. The first diabetic dog required about 11 to 12 units of insulin per day prior to implantation. As shown in FIG. 5A these implanted beads reversed hyperglycemia for over six weeks as evidenced by the immediate reversal of hyperglycemia (drop in plasma glucose level after implantation from about 650 mg/dl to about 150 mg/dl), and the maintenance of the plasma glucose level at about 125 mg/dl for the duration of the study, without the need for any external administration of insulin.

In addition, at one month after implantation, a bolus intravenous injection of glucose caused only a transient rise in blood glucose level to 300 mg/dl, which was normalized within about 1 hour (data not shown). Prior to implantation, the same test showed a sugar level of over 600 mg/dl and remained significantly hyperglycemic for the duration of the test (greater than 600). These pre- and post-implantation tests provide evidence that the animals are truly diabetic absent the implants.

The second diabetic dog required about 8 to 10 units of insulin per day prior to implantation. As shown in FIG. 5B these implanted beads reversed hyperglycemia for over 7 days as evidenced by the immediate drop in plasma glucose level after implantation from about 350 mg/dl to about 100 mg/dl, and the maintenance of the plasma glucose level at about 100 mg/dl for the duration of the study, without the need for any external administration of insulin.

In this study, a low dose of CsA was administered to each dog. CsA was administered at a dosage of 10 mg/kg/day for the first two weeks, and then dropped to 5 mg/kg/day. However, by 21 days, HPLC analysis of the dog's blood showed no detectable trace of CsA. Thus, the blood level of CsA was less than about 30 ng/ml, which is the lowest detectable limit of this measurement technique.

Factor IX Expressing Cells

HeLa cells, primary rabbit fibroblast cells (WHHL), and hepatoma cells (HepG2) were engineered to overexpress human Factor IX by transfection with one of two human Factor IX expressing retroviral sequences, Moloney murine Leukemia virus LTR (Mo-LTR) or Myeloproliferative sarcoma virus LTR (MPSV-LTR). Human FIX is expressed from the retroviral 5' LTR promotor, while the dominant selectable marker npt (neomycin phosphotransferase; neo resistance; G418 resistance) is expressed from an internal promoter. Three of the four cell populations (one of each of HeLa, WHHL, and HepG2) were generated with the same retroviral vector which uses the Mo-LTR The fourth population (WHHL) was generated using MPSV-LTR. All four cell populations secreted detectable levels of human FIX as determined by ELISA.

These cells were then encapsulated as follows. $1 \times 10^6$ or $2 \times 10^6$ cells were encapsulated in 800±100 μm diameter beads made from 1.0 ml of alginate. These beads were then cultured in vitro in DMEM in high glucose (G418 at a concentration of 0.8 mg/ml) to determine the amount of human Factor IX secreted by these encapsulated cells. The encapsulated cells produced high levels of Factor IX. Selection for G418 should be applied if the cells are grown for more than 2 ½ weeks in culture.

To determine the levels of Factor IX that these encapsulated cells produce in vivo, they are injected i.p. into mice. Untreated mice serve as controls. Plasma human Factor IX concentrations are measured at various time intervals after implantataion by tail bleedings using an enzyme immunoassay (Asserachrom IX:Ag; American Bioproducts).

Uses of Uncoated Gel Beads

The uncoated gel beads of the invention can be used to treat a variety of diseases that result from the defective or insufficient production of a particular enzyme or hormone by the body. In effect, the current methods provide a type of replacement therapy. A number of well-characterized disorders caused by the loss or malfunction of specific cells in the body are amenable to replacement therapy. For example, islets of Langerhans can be used for the treatment of diabetes, hepatocytes for hepatic failure, adrenal gland cells for Parkinson's disease, cells that produce nerve growth factor (NGF) for Alzheimer's disease, cells that produce factors VII and IX for hemophilia, and endocrine cells for treating disorders resulting from hormone deficiency, e.g. hypoparathyroidism Moreover, by using recombinant DNA methods, so-called "gene therapy," or encapsulating other tissues, it should also be possible to treat patients suffering from chronic pain, cancer (e.g., hairy cell leukemia, melanoma, and renal carcinoma), AIDS (treated by immunological augmentation), Kaposi's Sarcoma (treated by administration of interferon, IL-2, or TNF-α), primary hematologic disorders, patients with long-lasting aplasia, and patients who are myelosuppressed (treated by bone marrow transplantation and aggressive chemotherapy). Uncoated gel beads should also be useful in the treatment of affective disorders, Huntington's Disease, Duchenne's Muscular Dystrophy, epilepsy, infertility, spinal cord injuries, and in wound healing.

Implantation of specific cells can also serve to detoxify or to remove deleterious substances from the circulation. For example, the implantation of appropriate living cells restores normal physiologic function by providing replacement for the diseased cells, tissues, or organs, e.g., in hepatic encephalopathy (produced by liver disease) or uremia (produced by kidney failure).

In each application, a sufficient number of uncoated beads, containing the-desired living cells, are implanted into the patient, e.g., surgically or with a syringe. The beads are implanted, e.g., intraperitoneally, for a systemic effect, or into a particular location, e.g. the brain to treat Parkinson's disease, or the spinal cord to treat spinal cord injuries, for a local affect.

The dose of uncoated beads to be used is determined initially from results of in vitro studies. In addition, in vivo results in, e.g., mice, rats, or dogs will facilitate more accurate assessment of required doses, as these tests are generally predictive of efficacy in human patients. For example, spontaneous diabetes in dogs is considered to be similar to type 1 diabetes in man. Soon-Shiong et al., *Transplantation*, 54:769–774 (1992).

The beads are intended to remain in the patient with viable donor cells for extended periods of time up to several months or years. However, if it is determined that the donor cells are no longer viable, e.g., by monitoring the patient's blood for a certain level of the protein secreted by the donor cells, it is a simple task to renew the supply of beads in the patient.

Diabetes Mellitus

To treat diabetes, e.g., in a dog or human patient, the implantable beads preferably encapsulate isolated canine or porcine islets or other cells that produce insulin or insulin-like growth factor 1 (IGF-1). Islets are prepared and encapsulated using procedures described above. Insulin secretory activity of the encapsulated cells or islets is determined both in static culture, e.g., expressed per islet volume, and based on the capability of the islets to respond to graded concentrations of glucose. These values are established as described above. Once the insulin secretion activity of a particular batch of encapsulated islets is determined, the proper number of beads can be determined and implanted into a diabetic patient. For example, to treat a human patient that requires 20 to 50 units of insulin per day, the total number of beads should be selected to contain a total of about 10 to 2.5 million porcine islets. For beads designed to contain, on average, 20,000 islets/ml of gel, the proper dosage would be beads made from 50 to 125 ml of gel.

Hemophilia

Hemophilia is an X-linked hereditary bleeding disorder caused by Factor VIII or Factor IX deficiency. Recombinant methods have now been successfully used to create Factor VIII- and Factor IX-producing cells as described above. Encapsulation in uncoated gel beads and implantation of such cells according to the present invention can thus be used for an improved treatment for hemophilia.

Hepatic Diseases

Hepatocyte transplantation is useful not only for irreversible hepatic failure, but for several disease processes including hereditary enzyme abnormalities, acute hepatic failure, where the ability of the liver to regenerate may still exist, and as a bridge to whole liver transplantation in patients who develop sudden hepatic failure, either because of medical progression or because of rejection-related complications.

Wong and Chang, *Biomat. Art. Cells Art. Org.*, 16:731 (1988), have demonstrated the viability and regeneration of microencapsulated rat hepatocytes implanted into mice. Viable hepatocytes were microencapsulated in alginate-poly-(L-lysine) and implanted intraperitoneally into normal and galactosamine-induced liver failure mice. Eight days after implantation in the mice with induced liver failure, the viability of the encapsulated rat hepatocytes increased from 42% to nearly 100%. After 29 days, the viability of the encapsulated hepatocytes implanted in normal mice also increased from 42% to nearly 100%. By contrast, free rat hepatocytes implanted into mice all died within four or five days after xenotransplantation. The uncoated beads of the invention are well-suited to treat hepatic failure.

Other investigators have shown that microencapsulated hepatocytes continue the synthesis and secretion of many specific proteins and enzymes. Cai et al., *Hepatology*, 10:855 (1989), developed and evaluated a system of microencapsulation of primary rat hepatocytes. Urea formation, prothrombin and cholinesterase activity, the incorporation of tritiated leucine into intracellular proteins, and the immunolocation of synthesized albumin were monitored in culture. Despite gradual decreases in some of these activities, the encapsulated hepatocytes continued to function throughout the 35-day observation period. In addition, Bruni and Chang, *Biomat. Art. Cells Art. Org.*, 17:403 (1989), demonstrated the use of microencapsulated hepatocytes to lower bilirubin levels in hyperbilirubinemia. Microencapsulated hepatocytes were injected into the peritoneal cavity of Grunn rats. Bilirubin dropped from 14 mg/100 ml to 6 mg/100 ml, and remained depressed after 90 days. Again, the uncoated gel beads of the invention can be used as described above to treat these hepatic diseases.

Parkinson's Disease

Parkinson's disease is a neuronal system disease, involving a degeneration of the nigrostriatal dopaminergic system. Experimental work in both rodents and nonhuman primates has shown that transplantation of fetal tissue containing substantia nigra (dopaminergic) neurons from ventral mesencephalon to dopamine-depleted striatum reinstates near-normal dopamine innervation and reduces motor abnormalities. In addition, implantation of adrenal chromaffin cells has been shown to reverse chemically-induced Parkinson's disease in rodents.

Widner at al., *Transplant. Proc.*, 23:793 (1991), recently reported evidence of fetal nigral allograft survival and function up to 10 months after transplantation and immunosuppression (cyclosporine, azathioprine, and prednisone) in a human Parkinson's patient. Beginning from the second month after the transplantation, they observed a progressive decrease in limb rigidity, increased movement speed in a number of arm, hand, and foot movements, and prolonged "on" periods (>80% increase) after a single dose of L-dopa.

Thus, transplantation of fetal neural tissue, or cells genetically engineered to produce dopamine and nerve growth factors or other neurotropic factors, should have a great potential as a new therapeutic approach in patients with neurological disorders. However, in the case of transplanted xenogeneic donor tissue, rejection would pose a serious problem, even by the combined approach of using an immunoprivileged site and by employing immunosuppressive drugs. Therefore the uncoated beads of the invention permit a novel approach to this problem, i.e., the delivery of dopamine for the treatment of Parkinson's disease using encapsulated donor tissue harvested from animals or genetically engineered cells.

Alzheimer's Disease

An estimated 2.5 to 3.0 million Americans are afflicted with Alzheimer's disease. The disease is characterized by a progressive loss of cognitive function associated with degeneration of basal forebrain cholinergic neurons. Studies in animals indicate that Nerve Growth Factor (NGF), e.g., brain-derived neurotrophic factor (BDNF) and neurotrophin-3 (NT-3), available from Regeneron and Amgen, respectively, and other neurotropic factors normally act to support the viability and function of these neuron cells, and that continuous infusion of NGF into the ventricles can prevent injury-induced degeneration of cholinergic neurons as described in Williams et al., *P.N.A.S., USA*, 83:9231 (1986). This treatment correlates with improved cognitive function in rodents with memory impairment as described in Fisher et al., *Neurobiol. Aging*, 10:89 (1989).

These studies suggest that uncoated gel beads containing grafts of recombinant or natural NGF-secreting tissue such as astroglial cells or developing skin, can be used to treat patients suffering from Alzheimer's disease.

Gene Therapy

Gene therapy is an approach to treating a broad range of diseases by delivering therapeutic genes directly into the human body. Diseases that can potentially be cured by gene therapy include diseases associated with the aging population such as cancer, heart disease, Alzheimer's disease, high blood pressure, atherosclerosis and arthritis; viral infectious diseases such as acquired immune deficiency syndrome (AIDS) and herpes; and inherited diseases such as diabetes, hemophilia, cystic fibrosis, and muscular dystrophy.

In one particular example, a favored approach for human gene therapy involves the transplantation of genetically-altered cells into patients, e.g., as described Rosenberg, et al., *New Eng. J. Med.*, 323:570–578 (1988). This approach requires the surgical removal of cells from each patient to isolate target cells from nontarget cells. Genes are introduced into these cells via viral vectors or other means, followed by transplantation of the genetically-altered cells back into the patient. Although this approach is useful for purposes such as enzyme replacement therapy (for example, for transplantation into a patient of cells that secrete a hormone that diseased cells can no longer secrete), transplantation strategies are less likely to be suitable for treating diseases such as cystic fibrosis or cancer, where the diseased cells themselves must be corrected. Other problems commonly encountered with this approach include technical problems, including inefficient transduction of stem cells, low expression of the transgene, and growth of cells in tissue culture which may select for cells that are predisposed to cancer.

The uncoated particles of the invention are well suited to avoid these problems, because they allow the use of standard human cell lines of e.g., fibroblast cells, epithelial cells such as HeLa cells, and hepatoma cells such as HepG2, as the implanted cells, rather than requiring the surgical removal of cells from the patient. These cell lines are genetically altered as required by standard techniques and are encapsulated and implanted into the patient. These cell lines are much easier to obtain, culture, and work with than individual patients' cells. Moreover, since the uncoated particles prevent the patient's immune system from recognizing and attacking the implanted cells, any human cell lines can be used, making the technique of gene therapy more universally applicable.

Hypoparathyroidism

Acute and chronic symptoms of hypoparathyroidism result from untreated hypocalcemia, and are shared by both hereditary and acquired hypoparathyroidism. The hereditary form typically occurs as an isolated entity without other endocrine or dermatologic manifestations or, more typically, in association with other abnormalities such as defective development of the thymus or failure of other endocrine organs such as the thyroid or ovary. Acquired hypoparathyroidism is usually the result of inadvertent surgical removal of all the parathyroid glands, and is a problem in patients undergoing operations secondary to parathyroid adenoma or hyperplasia. Hypoparathyroidism has been treated in hypocalcemic rats by the administration of microencapsulated parathyroid cells that served as a bioartificial parathyroid. Parathyroid cells can also be encapsulated in the uncoated gel beads of the invention for use in administration to animal and human patients.

Osteoporosis

The term osteoporosis covers diseases of diverse etiology that cause a reduction in the mass of bone per unit volume. These diseases can be treated by the administration of uncoated gel beads containing cells that secrete insulin-like growth factor (IGF-1), estrogen in postmenopausal woman to reduce the negative calcium balance and decrease urinary hydroxyproline, androgens in the treatment of osteoporotic men with gonadal deficiency, or calcitonin for use in established osteoporosis.

Reproductive Disorders

There are numerous disorders of the ovary and female reproductive tract that can be treated with progestogens, estrogens, and other hormones. These include progestogen, e.g., progesterone, therapy to inhibit pituitary gonadotropins (precocious puberty in girls), and for prophylaxis to prevent hyperplasia in PCOD. Estrogen therapy is used in the treatment of gonadal failure, control of fertility, and in the management of dysfunctional uterine bleeding. Androgens, gonadotropins, and other hormones are used to treat disorders of the testis, e.g., androgen therapy in hypogonadal men, or gonadotropins to establish or restore fertility in patients with gonadotropin deficiency. Accordingly, these diseases can be treated with uncoated beads containing the appropriate hormone-producing cells.

Huntington's Disease

Huntington's disease is characterized by a combination of choreoathetotic movements and progressive dementia usually beginning in midadult life. Distinctive for the disease is atrophy of the caudate nucleus and, to a lesser extent, other structures of the basal ganglia (putamen and globus pallidus). Rodent cells that secrete neurotropic factors have been implanted into the brains of baboons that have a condition similar to Huntington's disease and reversed some of the damaged nerve networks that, in Huntington's patients, lead to progressive loss of control over the body. Similarly, Huntington's disease in human patients can be treated by the administration of uncoated beads that contain human or recombinant cells that secrete the appropriate neurotrophic factors.

Spinal Cord Injuries

The majority of spinal cord injuries result from damage to the surrounding vertebral column from fracture, dislocation, or both. Treatment of such injuries involves the administration of nerve growth factors such as ciliary neurotropic factor (CNTF), insulin-like growth factor (IGF-1), and neurotropic factors, to enhance the repair of the central and peripheral nervous system. Thus, uncoated gel beads containing cells that secrete such factors, either naturally or through genetic engineering, can be used to treat spinal cord injuries.

Mood (or Affective) Disorders

Mood disorders are a group of mental disorders such as schizophrenia characterized by extreme exaggerations and disturbances of mood and affect associated with physiologic (vegetative), cognitive, and psychomotor dysfunctions. Many mood disorders are associated with medical diseases that can be treated with uncoated gel beads containing the appropriate cells such as hypothyroidism, Parkinson's disease, Alzheimer's disease, and malignancies as discussed herein. In addition, it has been shown that the neurotransmitter 5-hydroxyindol acetic acid (5-HIAA), a serotonin metabolite, is reduced in the cerebral spinal fluid of depressed patients. Deficits in other neurotransmitters such as dopamine and gamma-aminobutyric acid (GABA) have also been identified in patients with major depression. Therefore, uncoated gel beads containing cells that secrete these neurotransmitter are useful to treat these deficiencies.

Motor Neuron Diseases

Degenerative motor neuron diseases include ALS (see above), heritable motor neuron diseases (spinal muscular atrophy (SMA), and those associated with other degenerative disorders such as olivopontocerebellar atrophies and peroneal muscular atrophy. These diseases can be treated by administration of uncoated gel beads containing cells that secrete neurotropic factors like brain-derived neurotrophic factor (BDNF), and neurotrophin-3 (NT-3).

Acquired Immunodeficiency Syndrome (AIDS)

AIDS is caused by an underlying defect in cell-mediated immunity due to the human immunodeficiency virus (HIV), and causes persistent constitutional symptoms and/or diseases such as secondary infections, neoplasms, and neurologic disease. Patients can be treated to ameliorate symptoms by immunologic augmentation with uncoated beads that contain cells genetically engineered to secrete, e.g., recombinant human IL-2 (to decrease suppressor cell activity resulting in an increased T cell adjuvant activity); or recombinant human IHF-γ (macrophage augmentation). AIDS-related tumors such as Kaposi's sarcoma can be treated with encapsulated cells that secrete human interferon-α, interleukin-2 and tumor necrosis factor (TNF)

Amyotrophic Lateral sclerosis (Lou Gehrig's Disease)

ALS is the most frequently encountered form of progressive motor neuron disease, and is characterized by progressive loss of motor neurons, both in the cerebral cortex and in the anterior horns of the spinal cord, together with their homologs in motor nuclei of the brainstem. ALS can be treated with uncoated beads that contain cells that secrete nerve growth factors such as myotrophin, insulin-like growth factor (IGF-1), ciliary neurotropic factor (CNTF), brain-derived neurotrophic factor (BDNF) and neurotrophin-3 (NT-3). Animal studies with these factors (IGF-1 is available from Cephalon, CNTF from Regeneron, and NT-3 from Amgen), have demonstrated that they can stem the degenerative effects caused by nerve damage or disease.

Cancer

In most cases, cancer originates from a single stem cell which proliferates to form a clone of malignant cells. Growth is not properly regulated by the normal biochemical and physical influences in the environment. There is also a lack of normal, coordinated cell differentiation. Cancer cells develop the capacity for discontinuous growth and dissemination to other parts of the body.

Various cancers can be treated according to the invention by the administration of uncoated gel beads containing cells that secrete interferon-α (IFN-α) (for solid tumors, hairy cell leukemia, Kaposi's sarcoma, osteosarcoma, and various lymphomas); recombinant interleukin-2 (IL-2) (for melanoma, renal carcinoma, and Kaposi's sarcoma); tumor necrosis factor (w/IL-2 for Kaposi's sarcoma); recombinant human IFN-α and recombinant human colony stimulating factor-granulocyte macrophage (CSF-gm) (for Kaposi's sarcoma), recombinant human INF-γ (for macrophage augmentation); CSF (for aggressive chemotherapy, bone marrow transplantation, priming of leukemic cells to enhance sensitivity to chemotherapy and to support dose intensification); ciliary neurotropic factor (CNTF) and insulin-like growth factor (IGF-1) (for peripheral neuropathies caused by chemotherapy); adrenal gland cells (for pain relief when injected into the lower spine to secrete natural painkillers) and progestogen-producing cells (for palliation in endometrial and breast carcinoma).

Duchenne's Muscular Dystrophy

Duchenne's dystrophy is an X-linked recessive disorder characterized by progressive weakness of girdle muscles, inability to walk after age 12, kyphoscoliosis (curvature of the spine), and respiratory failure after the fourth decade. This disease can be treated by administration of uncoated beads containing myoblast cells and growth factors. Myoblasts have been injected into young boys with Duchenne's muscular dystrophy to determine whether the cells can supply a structural protein that is missing. Researchers have observed muscle strength improvement in several of the boys.

Epilepsy

The epilepsies are a group of disorders characterized by chronic, recurrent, paroxysmal changes in neurologic function caused by abnormalities in the electrical activity of the brain. In some forms of focal epilepsy, inhibitory interneurons appear to be preferentially lost. Treatment with neurotropic factors and other neuropeptides such as has been found effective. Therefore the uncoated beads of the intention containing cells secreting these factors can be used to treat epilepsy Other Embodiments It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

What is claimed is:

1. A method of implanting a living donor cell into a host animal, wherein said animal is a mammal larger than a rat or mouse, with minimal inflammatory response or rejection of the donor cell by the host animal, said method comprising the steps of obtaining an uncoated particle comprising a biocompatible, temperature-independent gel that encapsulates the living donor cell, wherein said uncoated particle provides a molecular weight cutoff that prevents host animal immune cells from entering the particle, and does not prevent entry of host animal IgG and complement into said particle, wherein said particle has a diameter of 700–6,000 microns, and implanting the uncoated particle into the host animal.

2. A method of claim 1, wherein said donor cell is obtained from an species that is the same as the host animal.

3. A method of claim 2, wherein the host animal is a dog.

4. A method of claim 2, wherein the host animal is a human.

5. A method of claim 4, wherein the donor cell is a genetically altered human cell.

6. A method of claim 1, wherein the donor cell is obtained from an animal species that is different from the host animal.

7. A method of claim 6, wherein the host animal is a dog.

8. A method of claim 6, wherein the host animal is a human.

9. A method of claim 8, wherein the donor cell is a porcine, bovine, or canine cell.

10. A method of claim 8, wherein the donor cell is a pancreatic islet cell.

11. A method of claim 1, wherein the donor cell secretes Factor IX, Factor VIII, an interleukin, an interferon, or an endocrine hormone.

12. A method of claim 1, wherein the donor cell secretes a nerve growth factor, tumor necrosis factor alpha, a neurotropic factor, or a neurotransmitter.

13. A method of claim 1, wherein said gel particle is spherical and has a diameter of from 1,500–3,500 microns.

14. A method of claim 13, wherein said gel particle has a diameter of from 2000 to 4500 microns.

15. A method of claim 1, wherein said gel is an alginate or alginate derivative.

16. A method of claim 15, wherein said alginate is crosslinked with an ion.

17. A method of claim 16, wherein said alginate is crosslinked with a calcium salt.

18. A method of claim 1, wherein said uncoated gel particle is biodegradable.

19. A method of claim 18, wherein a rate of degradation of said gel in said uncoated particle is selected to match a life expectancy of said donor cell.

20. A method of claim 1, wherein said uncoated particle encapsulates an autologous erythrocyte in addition to the donor cell.

21. A method of claim 1, wherein said uncoated particle containing a living cell is treated with a nitric oxide inhibitor prior to implantation.

22. A method of claim 1, further comprising the step of administering a drug to the host animal at a dosage effective to inhibit fibrosis and inflammation around said uncoated particle, but at a dosage lower than that required to achieve immunosuppression when said donor cell is implanted into the host animal without encapsulation.

23. A method of claim 22, wherein said drug is cyclosporin A and is administered at a dosage that achieves a whole blood trough level of less than about 100 ng/ml in the host animal.

24. A method of claim 22, wherein said drug is administered for up to one month after implantation, and is then no longer administered.

25. A method of implanting a living donor cell into a host animal, wherein said animal is a mammal larger than a rat or mouse, with inflammatory response or rejection of the donor cell by the host animal, said method comprising the steps of suspending the living donor cell in a liquid medium, said medium comprising water and a biocompatible, temperature-independent liquid gel, forming a droplet of said liquid medium that contains at least one living cell, solidifying said droplet to form a gel particle that encapsulates the living cell, whereby no outer coating is formed on said particle, and wherein said uncoated particle provides a molecular weight cutoff that prevents host animal immune cells from entering the particle, and does not prevent entry of host animal IgG and complement into said particle, wherein said particle has a diameter of 700–6,000 microns and implanting the uncoated particle into the host.

26. A method of claim 25, wherein said liquid medium contains pancreatic islets.

27. A method of claim 25, wherein said pancreatic islets are contained in said liquid medium at a density of 10,000 to 35,000 islets per milliliter of said medium.

28. A method of claim 25, wherein said liquid medium contains living cells at a density of about $10^5$ to $10^8$ cells per milliliter of said medium.

29. A method of treating a disease in a patient, wherein said patient is a mammal larger than a rat or mouse, caused by a deficient production of a substance in the patient, said method comprising the steps of obtaining an uncoated particle comprising a biocompatible, temperature-independent gel that encapsulates a living donor cell that secretes said substance, wherein said uncoated particle provides a molecular weight cutoff that prevents patient immune cells from entering the particle, and does not prevent entry of patient IgG and complement into said particle, wherein said particle has a diameter of 700–6,000 microns, and implanting the uncoated particle into the patient in a location and in a manner that allows the living cell to remain physiologically active and secrete said substance into the patient to treat said disease.

30. A method of claim 29, wherein the donor cell is obtained from an animal species that is the same as the patient.

31. A method of claim 30, wherein the patient is a dog.

32. A method of claim 30, wherein the patient is a human.

33. A method of claim 32, wherein the donor cell is a genetically altered human cell.

34. A method of claim 29, wherein the donor cell is obtained from a species that is different from the patient.

35. A method of claim 34, wherein the patient is a dog.

36. A method of claim 34, wherein the patient is a human.

37. A method of claim 29, wherein the donor cell is a porcine, bovine, canine, bacterial, fungal, or plant cell.

38. A method of claim 29, wherein the disease is diabetes and the donor cell is a pancreatic islet cell.

39. A method of claim 29, wherein the donor cell secretes Factor IX, Factor VIII, an interleukin, an interferon, an endocrine hormone, a nerve growth factor, tumor necrosis factor alpha, a neurotropic factor or a neurotransmitter.

40. A method of claim 29, wherein the disease is diabetes mellitus, hepatic disease, amyotrophic lateral sclerosis, hemophilia, hypothyroidism, Parkinson's disease, acquired immune deficiency syndrome, Duchenne's muscular dystrophy, infertility, epilepsy, Huntington's disease, hypoparathyroidism, a mood disorder, a motor neuron disease, osteoporosis, or Alzheimer's disease.

41. A method of claim 29, wherein the gel particles are implanted into an immunoprivileged site in the patient.

42. An in vivo method of culturing a living cell, said method comprising the steps of encapsulating the living cell in an uncoated particle comprising a biocompatible, temperature-independent gel, inserting said uncoated particle into an animal, and allowing said animal to thrive, thereby culturing the cell wherein said animal is a mammal larger than a rat or mouse, wherein said particle has a diameter of 700–6,000 microns and wherein said uncoated particle provides a molecular weight cutoff that prevents host animal immune cells from entering the particle, and does not prevent entry of host animal IgG and complement into said particle.

43. An in vitro method of culturing a living cell, said method comprising the steps of encapsulating the living cell in an uncoated particle comprising a biocompatible, temperature-independent gel, wherein said particle has a diameter of 700–6,000 microns and wherein said uncoated particle provides a molecular weight cutoff that prevents host animal immune cells from entering the particle, and does not prevent entry of host animal IgG and complement into said particle placing said uncoated particle into a medium including nutrients and oxygen, and maintaining a sufficient amount of nutrients and oxygen in said medium to allow the cell to thrive, thereby culturing the cell.

44. A method of manufacturing uncoated, temperature-independent gel particles containing living cells consisting of the steps of suspending the living cells in a liquid medium, said medium comprising water and a biocompatible, temperature-independent, liquid gel, forming a droplet of said liquid medium, solidifying said droplet to form a gel particle that encapsulates the living cells, whereby no outer coating is formed on said particle, wherein said particle has a diameter of 700–6,000 μm and wherein said uncoated particle provides a molecular weight cutoff that prevents host animal immune cells from entering the particle, and does not prevent entry of host animal IgG and complement into said particle, and storing said gelled uncoated particles in a nutrient medium to maintain the viability of the living cells.

45. A method of claim 22, wherein said drug is a nonsteroidal anti-inflammatory drug.

46. A method of implanting a living donor cell into a host animal, wherein said animal is a mammal larger than a rat or mouse, with minimal inflammatory response or rejection of the donor cell by the host animal, said method comprising the steps of obtaining an uncoated particle comprising a biocompatible, temperature-independent gel that encapsulates the living donor cell, wherein said uncoated particle provides a molecular weight cutoff that prevents host animal immune cells from entering the particle, and does not prevent entry of host animal IgG and complement into said particle, implanting the uncoated particle into the host animal, and administering a drug to the host animal at a dosage effective to inhibit fibrosis and inflammation of the uncoated particle, but at a dosage lower than that required to achieve immunosuppression when the donor cell is implanted into the host animal without encapsulation.

47. A method of claim 46, wherein said donor cell is obtained from an species that is the same as the host animal.

48. A method of claim 46, wherein the host animal is a human.

49. A method of claim 46, wherein the donor cell is a genetically altered human cell.

50. A method of claim 46, wherein the donor cell is obtained from an animal species that is different from the host animal.

51. A method of claim 50, wherein the host animal is a human.

52. A method of claim 50, wherein the donor cell is a porcine, bovine, or canine cell.

53. A method of claim 46, wherein the donor cell is a pancreatic islet cell.

54. A method of claim 46, wherein the donor cell secretes Factor IX, Factor VIII, an interleukin, an interferon, or an endocrine hormone.

55. A method of claim 46, wherein the donor cell secretes a nerve growth factor, tumor necrosis factor alpha, a neurotropic factor, or a neurotransmitter.

56. A method of claim 46, wherein said gel particle is spherical and has a diameter of from 50 to 6000 microns.

57. A method of claim 46, wherein said gel is an alginate or alginate derivative.

58. A method of claim 46, wherein said drug is cyclosporin A and is administered at a dosage that achieves a whole blood trough level of less than about 100 ng/ml in the host animal.

59. A method of claim 46, wherein said drug is administered for up to one month after implantation, and is then no longer administered.

60. A method of claim 46, wherein said drug is a nonsteroidal antis inflammatory drug.

61. A method of claim 1, wherein said particle is other than a sphere.

62. A method of claim 25, wherein said particle is other than a sphere.

63. A method of claim 29, wherein said particle is other than a sphere.

64. A method of claim 46, wherein said particle is other than a sphere.

* * * * *